US006685626B2

(12) United States Patent
Wironen

(10) Patent No.: US 6,685,626 B2
(45) Date of Patent: Feb. 3, 2004

(54) COMPOSITIONS, DEVICES, METHODS, AND KITS FOR INDUCTION OF ADHESIONS

(75) Inventor: John F. Wironen, Alachua, FL (US)

(73) Assignee: Regeneration Technologies, Inc., Alachua, FL (US)

(*) Notice: Subject to any disclaimer, the term of this patent is extended or adjusted under 35 U.S.C. 154(b) by 0 days.

(21) Appl. No.: 09/776,404

(22) Filed: Feb. 2, 2001

(65) Prior Publication Data

US 2002/0107429 A1 Aug. 8, 2002

(51) Int. Cl.[7] .................................................. A61F 2/00
(52) U.S. Cl. ............................. 600/37; 600/29; 600/30
(58) Field of Search ............................. 600/37, 29, 30, 600/32; 128/839

(56) References Cited

U.S. PATENT DOCUMENTS

| | | | | |
|---|---|---|---|---|
| 3,988,782 A | * | 11/1976 | Dardik et al. .................... 3/1 |
| 4,243,652 A | * | 1/1981 | Francis ......................... 424/1 |
| 5,036,867 A | * | 8/1991 | Biswas ....................... 128/885 |
| 5,112,354 A | * | 5/1992 | Sires .......................... 623/16 |
| 5,219,895 A | | 6/1993 | Kelman et al. |
| 5,352,715 A | | 10/1994 | Wallace et al. |
| 5,354,336 A | | 10/1994 | Kelman et al. |
| 5,362,294 A | * | 11/1994 | Seitzinger |
| 5,549,904 A | | 8/1996 | Juergensen et al. |
| 5,700,479 A | * | 12/1997 | Lundgren ................... 424/435 |
| 5,752,974 A | | 5/1998 | Rhee et al. |
| 5,874,537 A | | 2/1999 | Kelman et al. |
| 5,891,457 A | | 4/1999 | Neuwirth |
| 6,034,088 A | | 3/2000 | Reeve et al. |
| 6,042,534 A | * | 3/2000 | Gellman et al. ............. 600/300 |
| 6,086,907 A | | 7/2000 | Goldberg et al. |
| 6,110,101 A | * | 8/2000 | Tihon et al. |
| 6,117,067 A | * | 9/2000 | Gil-Vernet ..................... 600/30 |
| 6,221,005 B1 | * | 4/2001 | Bruckner et al. .............. 600/30 |
| 6,245,082 B1 | * | 6/2001 | Gellman et al. |
| 6,258,055 B1 | | 7/2001 | McCrory et al. ............. 604/60 |
| 6,273,852 B1 | * | 8/2001 | Lethe et al. .................... 600/30 |
| 6,296,632 B1 | | 10/2001 | Lüscher et al. .......... 604/890.1 |
| 6,328,686 B1 | * | 12/2001 | Kovac ........................... 600/30 |
| 6,387,978 B2 | | 5/2002 | Rona et al. .................. 523/113 |
| 2002/0010457 A1 | | 1/2002 | Duchon et al. .............. 604/515 |
| 2002/0106411 A1 | | 8/2002 | Wironen et al. ............. 424/489 |

FOREIGN PATENT DOCUMENTS

| | | | | |
|---|---|---|---|---|
| EP | 0 797 988 A2 | | 10/1997 | |
| GB | WO-99/43271 | * | 9/1999 | ............. A61F/2/02 |
| WO | WO 96/23503 | | 8/1996 | |
| WO | WO 98/40113 | | 9/1998 | |

OTHER PUBLICATIONS

Annex to Form PCT/ISA/206, Communication Relating to the Results of the Partial International Search, dated Sep. 27, 2002.
PCT International Search Report, dated Dec. 4, 2002.
W.F. Polishuk, M.D. & J.G. Schenker, M.D., "Induction of Intrauterine Adhesions in the Rabbit With Autogenous Fibroblast Implants", Mar. 15, 1973, pp. 789–794.
J.G. Schenker & H. Yaffe, "Induction of Intrauterine Adhesions in Experimental Animals and In Women", Feb. 1978, pp. 261–266.
"An In Vitro Fibroblast–enriched Sponge Preparation for Induction of Intrauterine Adhesions", Aug. 1976, pp. 849–851.

* cited by examiner

*Primary Examiner*—Gene Mancene
*Assistant Examiner*—Frederick C. Nicolas
(74) *Attorney, Agent, or Firm*—McAndrews, Held & Malloy, Ltd.; Donald J. Pochopien

(57) ABSTRACT

Disclosed and claimed are compositions, devices, methods and kits that are useful in surgical procedures, specifically to induce adhesions for the purposes of stabilizing implants, closing apertures, and otherwise promoting the adhesion of implants and anatomical structures to one another. The invention pertains to a composition containing specific particulate components, wherein the particulates promote an inflammatory reaction that results in the formation of an adhesion.

32 Claims, 2 Drawing Sheets

COMPOSITIONS, DEVICES, METHODS, AND KITS FOR INDUCTION OF ADHESIONS

FIELD OF THE INVENTION

This invention relates to compositions, devices, methods and kits that are useful in surgical procedures, specifically to induce adhesions for the purposes of stabilizing implants, closing apertures, and otherwise promoting the adhesion of implants and anatomical structures to one another.

BACKGROUND OF THE INVENTION

In the medical art, an adhesion is "a band of scar tissue that binds together two anatomic structures that normally are separate from each other." (Mosby's Medical, Nursing, & Allied Health Dictionary, Ed. 5, 1998). An adhesion may form in the body as a result of surgery, most commonly in the abdomen, due to inflammation, or due to injury. As used herein, the term "adhesion" is used to define fibrous tissue induced to form between a surgically introduced implant and an adjacent body part (tissue or organ area), or between adjacent body parts.

The field of surgery has long recognized problems caused by undesired formation of surgical adhesions, and technologies and strategies have been developed to minimize, reduce, or repair deleterious surgical adhesions. Among examples of efforts to deal with the undesired effects of surgical adhesions are U.S. Pat. Nos. 6,034,088 (Reeve et al.) and 6,086,907 (Goldberg et al.).

In contrast to these inventions, some inventions are directed to specific methods for forming adhesions or adhesion-like binding for beneficial purposes. For instance, U.S. Pat. No. 5,549,904 (Juergensen et al.) discloses and claims a biological adhesive composition employing as the key ingredient a tissue transglutaminase enzyme. This enzyme has been found to promote adhesion between tissue surfaces. U.S. Pat. Nos. 5,219,895, 5,354,336, and 5,874,537 (all by Kelman et al.), disclosed and claimed specific collagen-based compositions and related methods, where the collagen was polymerizable. A collagen-based composition was applied to an area of a patient needing adhesion of adjacent tissues, and after application the collagen was polymerized to adhere the tissues. Polymerization could occur a number of ways, including through ultraviolet light exposure. The disclosures of these patents are hereby incorporated by reference to show the state of the art prior to this invention.

In contrast to the formation of undesired surgical adhesions, the present invention recognizes a need in the art to induce adhesions at specific regions for a range of surgically useful applications. In contrast to the above referenced patents by Juergensen et al. and Kelman et al., the adhesions of the present invention are promoted at specific sites by means of introducing one or more particulate materials that promote the formation of an adhesion, where that adhesion has characteristics similar to a non-intentionally formed adhesion. The particulate materials are presented in various compositions which may include adhesives, binders, promoters, and the like, and may also include enzymes. The primary purpose for such intentional adhesions is to assure proper attachment and alignment between an implant and a body part, or a body part and another body part. The present invention provides compositions, devices, methods, and kits to provide for the promotion of adhesions where such adhesions are beneficial.

For instance, in the surgical procedure of implanting a bladder sling, the procedure has been known to fail in its desired effect, namely to exert pressure against the urethra and the bladder, to alleviate or prevent incontinence. This failure can result from slippage of the sling adjacent the desired area. In such failure, a second operation may be required, resulting in additional risk, trauma, expense, and recovery period, still without assurance that subsequent slippage will not again render the procedure ineffective. Thus, the present invention provides devices, methods and compositions that promote the formation of one or more adhesions between the implant and the neck of the bladder or other implant material and biological structure.

One embodiment of the present invention is an implant that contains at least one area containing specific water-insoluble particles that induce formation of at least one adhesion. When such adhesion(s) develop, this greatly lessens the possibility of slippage of the sling or other implant, because the adhesion provides a substantial attachment between the implant and the intended contact area of the bladder or other biological structure. In a more general sense, the compositions, devices, methods, and kit of the present invention are utilizable in a number of applications, including the preparation of implants having specific areas with an adhesion-forming capability, and a range of surgical procedures where site-specific adhesion is desired and induced to form.

Other aspects of the present invention are also disclosed. Overall, the present invention represents an improvement in the field of implants, surgical materials, and surgery techniques. These improvements are mechanistically based on the conception of the usefulness of adhesion formation in specific applications, and the development of various means to accomplish formation of beneficial adhesions. However, it should be understood that the usefulness of the compositions, devices, methods, and kits for induction of adhesions disclosed herein is not to be construed as limited to this or on any proposed mechanism of the proposed physiological steps thought to be relevant to formation.

SUMMARY OF THE INVENTION

The present invention provides compositions, devices methods, and kits useful in the intentional promotion of adhesions. Novel materials, compositions, mixtures and methods are disclosed that promote the formation of adhesions when in contact with a tissue of a patient. Preparations for applying these materials so as to adhere to an implant, or in or on a tissue or organ area, are also disclosed. Methods of forming adhesions using these materials, mixtures, compositions and novel implants are also disclosed.

In one embodiment of this invention, a surgical implant is prepared, and the surgical implant comprises a generalized structure and at least one area treated with a preparation containing materials that promote an adhesion between that area and a tissue or organ region contacting that area. An associated surgical method places this implant in a patient in need thereof, such that an adhesion forms between the implant at that area and a specified tissue or organ region contacting that area.

Another embodiment of this invention is a method of preparing materials that promote an adhesion, and injecting a solution, slurry, mixture, or composition comprising that preparation into a tissue or organ, such that an adhesion subsequently forms. For instance, where it is desired to close the uterus for medical reasons, such solution and the like may be injected at or near the cervix, and consequent formation of an adhesion closes off the cervix, thereby closing the uterus.

Another embodiment of the present invention is a composition for application to a surgical implant, the composition preferably comprising hydroxyapatite particles and gelatin, where the gelatin adheres the hydroxyapatite particles to a desired section of an implant. In a preferred embodiment, for instance, this composition is applied to a center section of a bladder sling, that section being the area that would be placed next to the area of the urethra and bladder where an adhesion between the sling and that portion of the bladder sling is desired for stabilization.

Additional objects, advantages, and novel features of the invention will be set forth in part in the description which follows, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

The foregoing and other objects and advantages are attained by a variety of compositions, devices methods, and kits according to the present invention that are useful in the intentional promotion of adhesions.

Figure 1A:
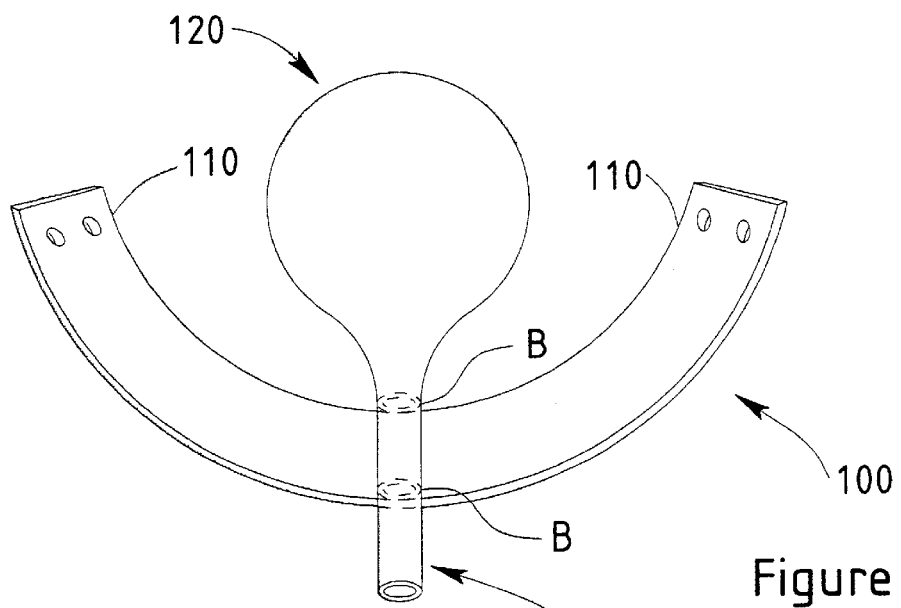
FIGS. 1A, B illustrate a possible outcome of a surgical implant of a urinary bladder sling not incorporating the present invention.

In accordance with one aspect of the invention, FIGS. 1A, B provide two diagrammatic perspective views of a urinary bladder sling of the prior art, which does not use the present invention. FIG. 1A shows a standard bladder sling, 100, having two ends for attachment, 110. The urethra, 115, coming from the bladder, 120, is shown in its proper position, in the center of the sling, 110. This typifies the position immediately after a surgical implant of the sling, which is implanted in order to apply pressure to a desired contact area of the urethra, 115, to thereby reduce or eliminate incontinence. This desired contact area is the bottom side of the span of the urethra, 115, between the lines B—B.

Figure 1B:
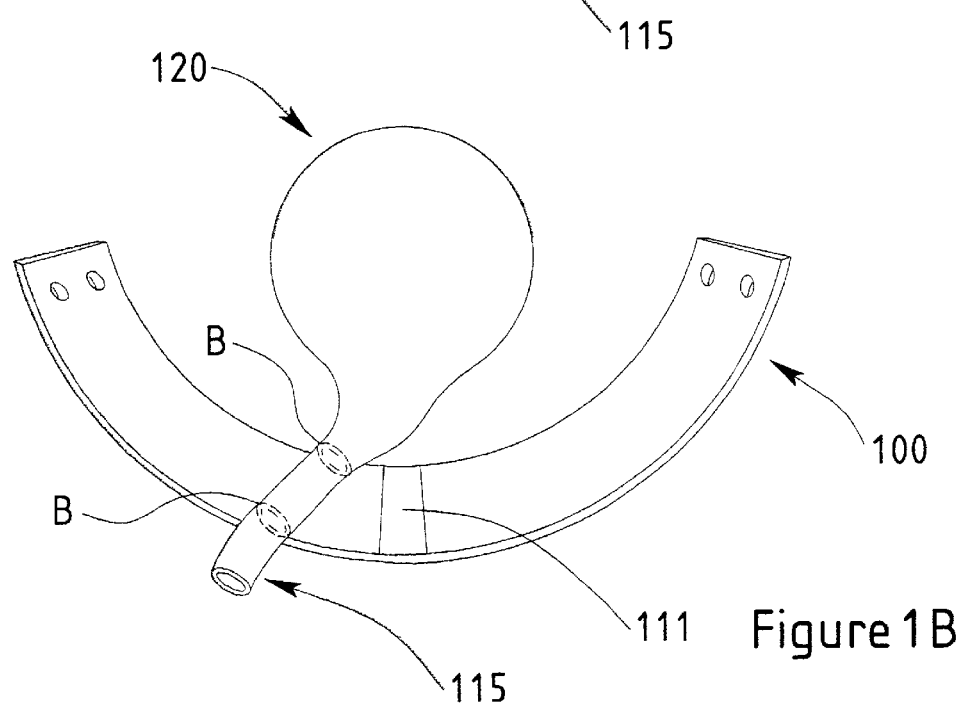

FIG. 1B illustrates a possible outcome of surgically implanting a typical implant not incorporating the present invention. Some time after surgery, the urethra, 115, and particularly the desired contact area, has slipped away from the intended alignment line, 111, between the sling, 100, and the urethra, 115. This results in less pressure against the urethra and consequently lower or no effectiveness in reducing or eliminating incontinence.

Figure 2A:
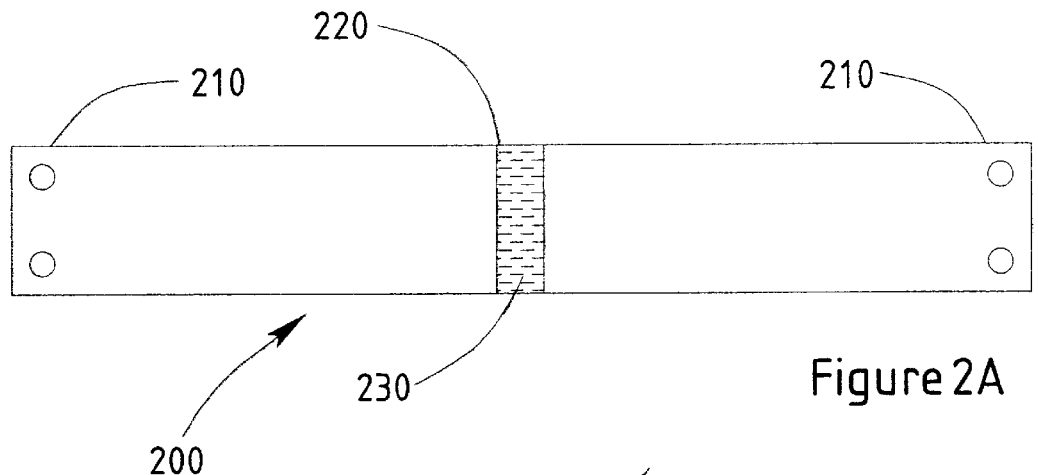
FIGS. 2A, B, C provide views of one embodiment of a urinary bladder sling according to the present invention, including two views of the sling once implanted into a living body where the methodology of the present invention has been applied to beneficial outcome.
Figure 2B:
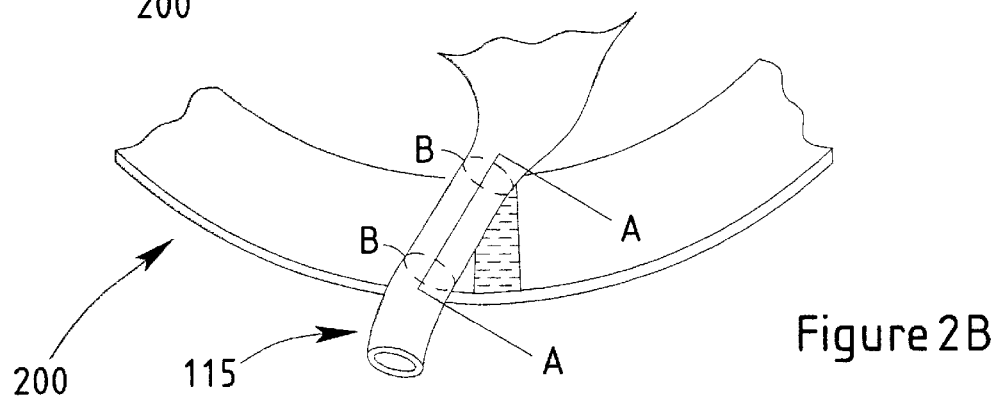
Figure 2C:
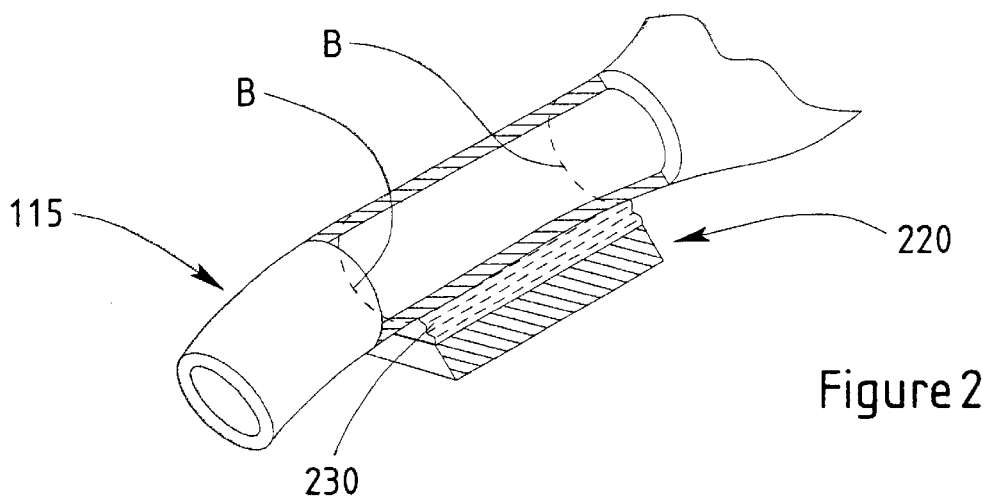

FIGS. 2A–C provide views of a urinary sling prepared according the present invention, and that sling's surgical implantation into a living body. FIG. 2A is a top view of urinary bladder sling, 200, an implant structure having two ends for attachment, 210, and a center area, 220, which contains an overlying layer of a composition containing adhesion-forming particulates according to the present invention. FIG. 2B is a perspective view of the sling, 200, in proper position under the desired contact area of the urethra, 115. In FIG. 2C, which provides a cross section along the A—A axis of FIG. 2B, the center area, 220, is shown with the now visible overlying layer, 230, of the composition containing adhesion-forming particulates according to the present invention. The overlying layer, 230, contacts the desired contact area of the urethra, 115. The composition promotes formation of an adhesion with the desired contact area. Once this adhesion is formed, the desired contact area remains adhered to the center area, 220, as a result of the activity induced by the overlying layer, 230. This contacting between the desired areas thereby effectively reduces or eliminates incontinence, with long-term stability and avoidance of slippage.

Another aspect of the present invention is a method of preparing an implant having at least one area containing an adhesion promoting preparation. The preparation is includes at least one material known to promote inflammation and, consequently an adhesion, and a carrier having the property of being adherable to an implant material, a tissue surface, and preferably, both an implant surface and a tissue surface. In the first step, one or more adhesion-promoting materials are combined with the carrier. Once well mixed, this preparation is applied to at least one specific area of an implant. When placed in a patient during a surgical procedure, each specific area so treated has the capability to induce the formation of an adhesion with an adjacent tissue or organ area with which that specific area is in contact.

The implant structure, being the body of the implant onto which the carrier and the adhesion-promoting material are applied, is formed for a range of functions known in the art. The composition of the implant structure may be selected from the non-exclusive group consisting of allograft tissue, xenograft tissue, autograft tissue, processed or semi-processed products made from allograft, xenograft or autograft tissue, biomaterials, metallic, polymeric (natural and synthetic), and combinations formed from these materials.

For the devices and the methods of the present invention, the adhesion-promoting material may be selected from or may be a combination of materials selected from the following non-exclusive list: fine particles of bone; fine particles of hydroxyapatite, in the 1 to 1,000 micrometers particle size range, preferably in the 1 to 70 micrometers particle size range; non-osteoinductive precipitated bone matrix (DBM), collagen particles that have been intentionally partially demineralized, preferably in the 1 to 70 micrometer particle size range; collagen shards, preferably in the 1 to 70 micrometer particle size range; insoluble salts, and talc. Cross-linked tissues, such as with glutaraldehyde may also be used for this purpose. Required characteristics of such material are: non-toxic, insoluble in water; and capable of inducing a mild inflammatory response to induce fibrosis. Preferred characteristics are that the material is biodegradable and will disappear in between 7 and 30 days of introduction into the person or animal. The preferred source of the bone, bone derivatives, and collagens is from human tissue, such as cadaveric tissue. Other possible sources are bovine, ovine, and other non-human cultured species. Combinations of these materials are also contemplated. Further, those skilled in the art will appreciate that a vast array of materials may meet this requirement and hence may be used according to this invention, even though not specifically mentioned herein.

It is noted, that throughout this specification, including the claims, by "particle size range" is meant that the median of the range of particle sizes for the middle 80 percent of the total particle mass falls within the specified range. That is to say, excluding the 10 percent of the smallest particles, and the 10 percent of the largest particles, on volume, number or mass basis, the median of the remaining smallest and largest particles falls within the specified numerical range. Thus, a 1 to 7 micrometers particle size range may include some particles smaller than 1-micrometer in maximum dimension, and some particles greater than 70 micrometers in maximum dimension, but the median of the majority of the particles falls within the 1 to 7 micrometers range.

For the devices and the methods of the present invention, the carrier may be selected from or may be a combination of materials selected from the following non-exclusive list: collagen; gelatin; carboxymethyl cellulose; hyaluronic acid; polyvinyl alcohol; thrombin; fibrin; albumin; and mucoadhesive polysaccharides such as chitosan, polyalcohols, polyamines, polyvinyls, polyamides, polyesters, polyanhydrides, polyorthosters, polyurethanes, polycarbonates, polyphosphazines, and polysilicates. Also, the composition may contain, for example in the carrier, growth factors including but not limited to PDGF, FGF, VEGF, BMP, and antibiotics. Required characteristics of the carrier are: non-toxic; able to suspend particles of adhesion promoting materials during application onto an implant; sets in or onto implant without undue spreading; and upon setting adheres the particles to the implant. Typically, the carrier preparation including the adhesion-promoting material is applied to the implant material, in advance of an operation, in the form of a foam or sheet. Combinations of these materials are also contemplated. Adherence of the carrier to tissue surfaces is also beneficial according to some embodiments of this invention.

Another aspect of the invention is a surgical implant, such as that prepared according to the foregoing method. The surgical implant, shown in FIG. 2, comprises a general structure, 1, having the desired shape, thickness, and characteristics of an implant for its intended purpose. For example, the surgical implant has a middle top section of a linear generalized structure. Examples of sources of the generalized structure include allograft tissue, xenograft or autograft tissue, biomaterials, metallic implants, ceramic implants, bone, demineralized bone, hydroxyapatite, synthetics, such as polylactic acid and combinations formed from these materials. By biomaterials is meant materials that are specifically adapted for use within a human being or animal, having the characteristic of being biocompatible for the application.

The surgical implant shown in FIG. 2 also comprises, as a key feature, at least one specialized area into or onto which are adhered water-insoluble particles that promote the formation of an adhesion. In the specific embodiment shown in FIG. 2, which is a bladder sling, one specialized area, 220, is positioned central and dorsal on the general structure, 200, at a point where the bladder sling is intended to remain adhered to the bladder or urethra.

In the application of the sling shown in FIG. 2, when the bladder sling is placed into a patient to control incontinence, the specialized area contacts the bladder neck. As a result of the bladder neck being in contact with the particles of the adhesion-promoting material(s) adhered in or on the specialized area, an adhesion forms. This adhesion holds the implant in the desired position, without slippage, to better ensure long-lasting results. Slippage, such as may occur without the adhesion may result in poor functional results of the operation, and the possible need for additional corrective surgeries.

A preferred embodiment of the present invention is a specific composition that promotes the formation of an adhesion, and which is applied to an area of an implant for that purpose. This composition comprises hydroxyapatite particles in the size range of 1 to 1,000 micrometers, preferably in the 1 to 70 micrometers particle size range, generally having sharp points. The composition, including the hydroxyapatite particles, should degrade within 10 years, and preferably degrades between 7 and 30 days after implantation. In one embodiment, the particles are suspended in an adherent composition, such as but not limited to, gelatin. Typically the gelatin is made into an aqueous solution having a 1 to 70 percent gelatin weight/total weight concentration, preferably 25 to 40 percent concentration, and the hydroxyapatite particles are mixed into this solution to form a suspension. Upon application to a specific area of an implant, the gelatin provides adhesive properties to bind the particles to the implant.

In a further application of the present invention, the composition of hydroxyapatite particles and gelatin is applied to a center top area of a urinary bladder sling, in a place where, upon implantation, the that area is adjacent to and comes in contact with the neck of the bladder, and consequently the formation of an advantageous adhesion between the neck of the bladder and the treated area of the implant is promoted. More broadly, this composition may be utilized for application to areas that promote adhesions on a wide range of surgical implants for a range of surgical procedures in which a specific, localized adhesion is desired. For example, one specific surgical procedure to benefit from the present invention is a "reversible vasectomy". Here an injection of a composition of the present invention is injected into a small area of the vas deferens, resulting in a blockage that later could be removed. Another example is blockage of arteriovenous malformations, as by injection of a composition according to the present invention.

Another embodiment of the present invention is a method of forming an adhesion by the steps of:

1. preparing a preparation of particles that, upon placement in a living body, promotes formation of an adhesion, and
2. injecting a quantity of said composition into a body area.

The injection into the body area promotes formation of an adhesion in the area of the injecting. Multiple injections may be given at one time, in different body areas, to promote a number of adhesions.

A further embodiment is to prepare the particles in an aqueous solution of gelatin, to form a suspension for injecting. A further embodiment is to inject the preparation using a syringe.

Depending on the site of injection, this method may result in the narrowing or the closure of a body opening. For instance, where it is medically desirable or necessary to close the cervical opening of the uterus, an injection of the preparation at or near the cervical opening results in adhesion formation (or scar tissue formation) that closes the uterus. More broadly, this method can be applied to a wider range of medical conditions where it is desirable to close or narrow an opening.

In accordance with another aspect of the invention, a method of promoting formation of an adhesion following a surgical procedure is achieved by the steps of:

1. preparing or obtaining an implant having at least one specialized area having material with adhesion-promoting properties, and
2. surgically placing the implant in a patient, so that each at least one specialized area is positioned adjacent to a tissue or organ area of the patient on which adhesion formation is desired with the specific at least one specialized area.

As a consequence of situating a specialized area next to a tissue or organ area onto which it is desired to form an adhesion with the implant specialized area, the promotion of an adhesion is achieved.

It is noted that, depending on the nature of the surgery and the anatomy and condition of the patient, certain procedures may be used to assure the correct positioning, at least until the adhesion is formed. For instance, temporary sutures or other means, such as adhesives, or the application of one or more enzymes that promote a binding of adjacent structures, such as by enzymatic catalysis, may be used to maintain the desired juxtaposition during formation of an adhesion. Specifically, U.S. Pat. No. 5,549,904 (Juergensen et al.) is incorporated by reference regarding a biological adhesive composition employing as the key ingredient a tissue transglutaminase enzyme. This enzyme has been found to promote adhesion between tissue surfaces by catalyzing the reaction between glutaminyl residues and amine donors. Such technology is applied by incorporating into the implant glutaminyl residues and/or amine donors near or in the implant area(s) having an adhesion promoting preparation or composition according to the present invention.

Also, U.S. Pat. Nos. 5,219,895, 5,354,336, and 5,874,537 (Kelman et al.), are incorporated by reference regarding disclosed and claimed specific collagen-based compositions and related methods, where the collagen is polymerizable. Collagens such as these may be used as adhesives to provide attachment points in or around an adhesion promoting preparation or composition according to the present invention. Upon inducing polymerization of the collagen, this adhesive system maintains the desired juxtaposition during formation of an adhesion according to the present invention.

It is noted that FIGS. 2A–C depicting this invention are merely representative of particular embodiments and are not meant to limit the range of possible configurations to which this invention may be applied. The features are represented and described by numbers consistent from drawing to drawing, where possible.

Having generally described this invention, including the best mode thereof, those skilled in the art will appreciate that the present invention contemplates the following embodiments, and equivalents thereof. However, those skilled in the art will appreciate that the scope of this invention should be measured by the claims appended hereto, and not merely by the specific embodiments exemplified herein.

What is claimed is:

1. A surgical implant comprising:
   a. a generalized structure prepared from the group consisting of allograft, xenograft, autograft, processed or semi-processed products made from allograft, xenograft or autograft tissue, biomaterials, metals, synthetic polymers, and combinations thereof; and
   b. at least one sectioned adhesion-promoting area within said generalized structure comprising water-insoluble particles,
   wherein, at the site of implantation of said surgical implant, each sectioned adhesion-promoting area produces an adhesion to tissue in contact with said sectioned adhesion-promoting area.

2. The implant according to claim 1, wherein said water-insoluble particles are selected from the group consisting of fine particles of bone, fine particles of hydroxyapatite, non-osteoinductive demineralized bone matrix, collagen shards, insoluble salts, and talc.

3. The implant according to claim 1, wherein said generalized structure is linearly shaped.

4. The implant according to claim 3, which is a bladder sling.

5. The implant according to claim 4, wherein said sectioned adhesion-promoting area is positioned at the middle top section of said bladder sling.

6. The implant according to claim 5, wherein said sectioned adhesion-promoting area is adhered to the lower apical neck of the bladder upon implantation of said surgical implant.

7. The implant according to claim 2, wherein said fine particles of hydroxyapatite range in particle size from 1 micrometer to 1,000 micrometers.

8. The implant according to claim 7, wherein said fine particles of hydroxyapatite range in particle size from 1 micrometer to 70 micrometers.

9. The implant according to claim 2, wherein said collagen shards range in particle size from 1 micrometer to 70 micrometers.

10. A method of promoting the formation of an adhesion comprising:
    a. preparing a composition comprising water insoluble particles that promote formation of an adhesion, and
    b. injecting a quantity of said composition into a specified area of a living body,
    wherein said water-insoluble particles are selected from the group consisting of fine particles of bone, fine particles of hydroxyapatite, non-osteoinductive demineralized bone matrix, collagen shards, insoluble salts, and talc; and whereby an adhesion is formed at said specified area.

11. The method according to claim 10, wherein the adhesion closes off an opening at or near the body area receiving the quantity of said composition.

12. The method according to claim 10, wherein said composition comprises an aqueous gelatin solution suspended with ground bone fragments, wherein said bone fragments do not induce formation of new bone.

13. The method according to claim 10, wherein the injecting is done with a syringe.

14. The method according to claim 11, wherein said body area is the entrance of the uterus.

15. The method according to claim 14, wherein injection of said composition at or near the entrance of the uterus produces a closure of said entrance of the uterus.

16. A method of promoting formation of at least one adhesion comprising:
    a. preparing or obtaining an implant having at least one sectioned adhesion-promoting area, said area comprising a particulate material with adhesion-promoting properties affixed thereto, and
    b. surgically placing said implant in a living body wherein each said sectioned adhesion-promoting area is positioned adjacent to a specified tissue or organ area of said living body on which adhesion formation is desired,
    whereby formation of an adhesion is promoted between each said sectioned adhesion-promoting area and said specified tissue or organ area in said living body.

17. The method according to claim 16, additionally comprising:
    c. affixing each sectioned adhesion-promoting area to each adjacent specified tissue or organ area, thereby stably positioning said specified tissue or organ area during the formation of an adhesion.

18. The method according to claim 17, wherein step (c) comprises suturing each sectioned adhesion-promoting area to each adjacent specified tissue or organ area.

19. The method according to claim 17, wherein step (c) further comprises inducing at least one enzyme that promotes adhesion through enzymatic catalysis.

20. The method according to claim 19, wherein said enzyme is transglutaminase.

21. The method according to claim 17, wherein step (c) is performed by using a polymerizable collagen.

22. A kit for implanting an implant that will form an adhesion with a tissue or organ in a living body, comprising:
   a. an implant comprising an implant structure having at least one sectioned adhesion-promoting area that is a means for formation of an adhesion to a tissue or organ of the living body; and
   b. instructions for placement of said implant, wherein upon proper surgical implantation, said at least one sectioned adhesion-promoting area forms at least one adhesion with at least one portion of a tissue or organ of the living body.

23. An implant for treating incontinence in a patient having a bladder and a urethra comprising an elongated structure having two opposing ends for attachment in proximity to said bladder in said patient, said elongated structure having a first portion which contacts the urethra at the neck of said bladder in said patient, said first portion having thereon at least one sectioned adhesion-promoting area comprising adhesion forming particulates in a carrier for forming an adhesion between said first portion of said implant and said urethra at the neck of said bladder, whereby said implant applies pressure to said urethra without slippage.

24. The implant of claim 23, wherein said particulates have sharp points.

25. The implant of claim 24, wherein said particulates have a particle size from 1 micrometer to 1,000 micrometers (microns).

26. The implant of claim 25, wherein said particulates are hydroxyapatite.

27. The implant of claim 24, wherein said carrier is gelatin.

28. The implant of claim 23, wherein said elongated material is an allograft, xenograft, or autograft.

29. The implant of claim 24, wherein the particulate is collagen shards.

30. The implant of claim 24, wherein the particulate is particles of bone.

31. The implant of claim 29, wherein the collagen shards have a size range of 1 micrometer to 70 micrometers.

32. The implant of claim 30, wherein the particles of bone have a size range of 1 micrometer to 70 micrometers.

* * * * *